US009861771B2

United States Patent
Brand et al.

(10) Patent No.: US 9,861,771 B2
(45) Date of Patent: *Jan. 9, 2018

(54) DEVICE HOUSING FOR AN AEROSOL CONTAINER

(71) Applicant: GLAXO GROUP LIMITED, Brentford, Middlesex (GB)

(72) Inventors: Peter John Brand, Ware (GB); James William Godfrey, Ware (GB); Paul Kenneth Rand, Ware (GB); Duncan Robertson, Perth (AU)

(73) Assignee: Glaxo Group Limited, Brentford, Middlesex (GB)

(*) Notice: Subject to any disclaimer, the term of this patent is extended or adjusted under 35 U.S.C. 154(b) by 0 days.

This patent is subject to a terminal disclaimer.

(21) Appl. No.: 15/053,498

(22) Filed: Feb. 25, 2016

(65) Prior Publication Data

US 2016/0166784 A1    Jun. 16, 2016

Related U.S. Application Data

(63) Continuation of application No. 12/705,821, filed on Feb. 15, 2010, now abandoned, which is a
(Continued)

(30) Foreign Application Priority Data

Oct. 16, 1999    (GB) .................................. 9924468.3
Aug. 22, 2000   (GB) .................................. 0020538.5

(51) Int. Cl.
*A61M 11/00*     (2006.01)
*A61M 15/00*     (2006.01)
(Continued)

(52) U.S. Cl.
CPC ........ *A61M 15/009* (2013.01); *A61M 15/008* (2014.02); *A61M 15/0051* (2014.02);
(Continued)

(58) Field of Classification Search
CPC ............ A61M 15/0065; A61M 15/009; A61M 15/0051; A61M 15/0068; A61M 15/008;
(Continued)

(56) References Cited

U.S. PATENT DOCUMENTS 1,638,209 A    8/1927  Niebuhr
2,841,190 A *  7/1958  Scheck .................. B65D 83/42
                                                      141/20
(Continued)

FOREIGN PATENT DOCUMENTS

DE         887716      8/1953
FR         2743055     7/1997
(Continued)

OTHER PUBLICATIONS

Penton Inc., Waldes Truarc Retaining Ring, Machine Design (1989) 61(1):161.

*Primary Examiner* — Steven Douglas
(74) *Attorney, Agent, or Firm* — James P. Riek; William R. Majarian

(57) ABSTRACT

An assembly having: a container configured to contain a product, the container having an end having a dispensing end surface, a central axis which extends through the end, and a neck underneath the end, the neck having an outer surface which tapers outwardly away from the central axis as it extends in a direction towards the end; an accessory non-removably mounted on the end of the container, the accessory having a surface bearing against the dispensing end surface of the container, and a sleeve disposed about the neck so that an inner surface of the sleeve is in facing
(Continued)

relation with the neck outer surface, and; an annular collar wedged between the sleeve inner surface and the neck outer surface and joined to the sleeve inner surface by a permanent joint.

4 Claims, 5 Drawing Sheets

Related U.S. Application Data continuation of application No. 10/373,950, filed on Feb. 26, 2003, now Pat. No. 7,661,423, which is a continuation of application No. 10/110,611, filed as application No. PCT/EP00/09991 on Oct. 11, 2000, now abandoned.

(51) Int. Cl.
  *A61M 16/16* (2006.01)
  *A61M 16/20* (2006.01)
  *A61M 16/00* (2006.01)
  *A61J 7/04* (2006.01)

(52) U.S. Cl.
  CPC ...... *A61M 15/0068* (2014.02); *A61M 16/161* (2014.02); *A61M 16/20* (2013.01); *A61J 7/0418* (2015.05); *A61M 2016/0036* (2013.01); *A61M 2205/3306* (2013.01); *A61M 2205/3368* (2013.01); *A61M 2205/3553* (2013.01); *A61M 2205/3584* (2013.01); *A61M 2205/52* (2013.01); *A61M 2205/60* (2013.01); *A61M 2205/6018* (2013.01); *A61M 2205/6054* (2013.01); *A61M 2205/8206* (2013.01); *A61M 2209/06* (2013.01); *A61M 2230/42* (2013.01); *A61M 2230/43* (2013.01); *A61M 2230/432* (2013.01); *A61M 2230/435* (2013.01); *A61M 2230/63* (2013.01); *Y10T 29/49826* (2015.01)

(58) Field of Classification Search
  CPC .. A61M 2016/0036; A61M 2205/3306; A61M 2205/3368; A61M 2205/3553; A61M 2205/3584; A61M 2205/52; A61M 2205/60; A61M 2205/6018; A61M 2205/6054; A61M 2205/8206; A61M 2209/06; A61M 2230/42; A61M 2230/43; A61M 2230/432; A61M 2230/435; A61M 2230/63; B65D 83/40; B65D 83/14; A61J 7/0418; Y10T 29/49826
  USPC ............ 128/200.14, 200.22–200.23; 222/30, 222/36–38; 239/71, 289, 337–339
  See application file for complete search history.

(56) References Cited

U.S. PATENT DOCUMENTS

| | | | |
|---|---|---|---|
| 3,104,034 A * | 9/1963 | Sagarin | B65D 83/205 137/382 |
| 3,120,318 A | 2/1964 | Rigor | |
| 3,184,115 A * | 5/1965 | Meshberg | A61M 15/009 128/200.23 |
| 3,185,349 A | 5/1965 | Sagarin | |
| 3,446,522 A | 5/1969 | Hoard | |
| 3,549,055 A | 12/1970 | Gatland | |
| 3,592,364 A | 7/1971 | Thornton | |
| 3,604,491 A * | 9/1971 | Spiess | B65D 75/5883 383/104 |
| 3,773,227 A | 11/1973 | Liang et al. | |
| 3,853,413 A | 12/1974 | Parran | |
| 3,904,061 A | 9/1975 | Keeler | |
| 3,915,348 A | 10/1975 | Suhr | |
| 3,935,877 A | 2/1976 | Franceschi | |
| 3,935,999 A | 2/1976 | Weyn | |
| 3,964,634 A | 6/1976 | Jasinski et al. | |
| 3,988,186 A | 10/1976 | Anderson | |
| 4,151,779 A | 5/1979 | Timmer | |
| 4,662,542 A | 5/1987 | Vitale | |
| 4,940,966 A | 7/1990 | Pettigrew et al. | |
| 5,060,643 A | 10/1991 | Rich et al. | |
| 5,069,368 A | 12/1991 | Godard et al. | |
| 5,082,129 A | 1/1992 | Kramer | |
| 5,175,043 A | 12/1992 | Yabe et al. | |
| 5,221,576 A | 6/1993 | Bose et al. | |
| 5,333,106 A | 7/1994 | Lanpher et al. | |
| 5,335,823 A | 8/1994 | Fuchs et al. | |
| 5,363,842 A | 11/1994 | Mishelevich et al. | |
| 5,435,282 A | 7/1995 | Haber et al. | |
| 5,460,171 A * | 10/1995 | Pesenti | A61M 15/0096 128/200.14 |
| 5,482,030 A | 1/1996 | Klein | |
| 5,544,647 A | 8/1996 | Jewett et al. | |
| 5,564,414 A | 10/1996 | Walker et al. | |
| 5,623,920 A | 4/1997 | Bryant | |
| 5,833,066 A | 11/1998 | Hargus et al. | |
| 5,878,917 A | 3/1999 | Reinhard et al. | |
| 5,954,232 A | 9/1999 | Shervington et al. | |
| 5,988,496 A | 11/1999 | Bruna | |
| 6,000,394 A | 12/1999 | Blaha-Schnabel et al. | |
| 6,029,659 A | 2/2000 | O'Connor | |
| 6,065,474 A | 5/2000 | Coe | |
| 6,076,521 A | 6/2000 | Lindahl et al. | |
| 6,082,358 A | 7/2000 | Scarrott et al. | |
| 6,119,684 A | 9/2000 | Nohl et al. | |
| 6,161,724 A | 12/2000 | Blacker et al. | |
| 6,170,717 B1 | 1/2001 | Di Giovanni et al. | |
| 6,190,326 B1 | 2/2001 | McKinnon et al. | |
| 6,234,168 B1 | 5/2001 | Bruna | |
| 6,398,132 B1 | 6/2002 | Junkel et al. | |
| 6,415,784 B1 | 7/2002 | Christup et al. | |
| 6,415,785 B1 | 7/2002 | Stage | |
| 6,516,799 B1 | 2/2003 | Greenwood et al. | |
| 6,561,384 B2 | 5/2003 | Blacker et al. | |
| 6,565,743 B1 | 5/2003 | Poirier et al. | |
| 6,578,573 B2 | 6/2003 | Koch | |
| 6,659,307 B1 | 12/2003 | Stradella | |
| 6,949,154 B2 * | 9/2005 | Hochrainer | A61J 3/072 156/272.8 |
| 6,997,349 B2 | 2/2006 | Blacker et al. | |
| 7,008,325 B2 | 3/2006 | Bongartz et al. | |
| 2003/0075175 A1 | 4/2003 | Helgesson et al. | |
| 2003/0136800 A1 | 7/2003 | Brand et al. | |
| 2006/0096594 A1 | 5/2006 | Bonney et al. | |

FOREIGN PATENT DOCUMENTS

| | | |
|---|---|---|
| GB | 2263873 | 8/1993 |
| JP | 1-154143 | 6/1989 |
| JP | 9058764 | 4/1997 |
| JP | 9104485 | 4/1997 |
| WO | 8602275 | 4/1986 |
| WO | 9212402 | 7/1992 |
| WO | 9631790 | 10/1996 |
| WO | 9856444 | 12/1998 |
| WO | 9906303 | 2/1999 |
| WO | 9936115 | 7/1999 |
| WO | 0016837 | 3/2000 |
| WO | 0053247 | 9/2000 |
| WO | 0128887 | 4/2001 |
| WO | 2004001664 | 12/2003 |

* cited by examiner

DEVICE HOUSING FOR AN AEROSOL CONTAINER

RELATED APPLICATIONS

This application is a continuation of U.S. patent application Ser. No. 12/705,821, filed Feb. 15, 2010, now abandoned, which is a continuation of U.S. patent application Ser. No. 10/373,950, filed Feb. 26, 2003, now U.S. Pat. No. 7,661,423, which is a continuation of U.S. patent application Ser. No. 10/110,611 filed Apr. 15, 2002, now abandoned, which is a United States National Phase Application, filed under 35 USC 371, of International Patent Application Serial No. PCT/EP00/09991 filed Oct. 11, 2000, which claims priority from GB 9924468.3 filed 16 Oct. 1999 and GB 0020538.5 filed Aug. 22, 2000, both in the United Kingdom.

TECHNICAL FIELD

The present invention relates to a housing for a mechanical or electrical device which is joinable to a collar affixed around the neck of an aerosol canister to form a chemical dispenser. In particular, it relates to a medicament dispenser formable by welding a housing for a dose counter to a collar affixed around the neck of an aerosol canister.

BACKGROUND TO THE INVENTION

Aerosol canisters are widely used in domestic, commercial and industrial situations for the application of a range of chemicals. Typical examples of chemical products which are dispensable in this way include cosmetics, health products, paints, pharmaceuticals and agrochemicals. Frequently there is a need to attach mechanical or electrical devices to such aerosol canisters, for example to regulate or record the flow of chemical from the canister, or to act as environmental sensors. Such devices may be affixed to the canisters by a range of technologies including the use of adhesives and heat treatment, such as soldering or welding. However, the attachment of such devices to aerosol canisters poses difficulties in terms of producing a secure joint without affecting the integrity of the chemical by the application of excess heat during the heating or welding process. Similarly, the use of adhesives may lead to contamination problems due to the presence of low concentrations of volatiles from the adhesive on dispensing the chemical.

Medicament dispensers are extensively used in the administration of medicines, particularly those for the treatment of respiratory disorders. Medicaments which are contained in an aerosol and are administered to a patient by means of an inhalation device are widely used in such therapy. These inhalation devices typically comprise a tubular housing or sleeve in which the aerosol canister is located and an outlet tube leading from the housing. The aerosol canisters used in such inhalation devices are designed to deliver a predetermined dose of medicament upon actuation; the valves can be opened either by depression of the valve member itself or by depression of the canister while the valve member is held stationary. In the use of such devices, the aerosol canister is placed in the tubular housing with the outlet valve member of the canister communicating via a support with the outlet tube, for example a nozzle or mouthpiece.

A recent development in this field of technology is the use of mechanical or electrical dose counters to register the number of medicament doses used or remaining within the medicament dispenser. Dose counters can be positioned within the tubular housing and operate by means of detecting movement of the housing relative to the aerosol canister on actuation of the dispenser by the patient. The indexing mechanism of the dose counter registers the actuation of the dispenser and the counter displays how many doses have been used or remain within the aerosol canister.

Some dose counters are detachable from the aerosol dispenser. One disadvantage of such devices is that the individual components may become separated and used in isolation from each other. Another disadvantage of these devices is that once the dose counter is removed from the aerosol canister it may be tampered with, typically by young children, to give a false reading. Detachment of the dose counter from the aerosol canister could therefore result in false readings on re-attachment to the canister. Furthermore, with patients having several different inhalers, the indicating device could be re-attached to the wrong dispenser.

Other dose counters are essentially irreversibly attached to the aerosol dispenser. One means of affixing dose counters to aerosol canisters is to use a 'snap-fit' mechanism whereby a tubular grip assembly on the dose counter housing is pushed into position around the neck of the valve ferrule thereby locking the two components together. Whilst this arrangement holds the two structures securely together there can, on occasions, be some lateral movement or 'play' of one component relative to the other. As mechanical dose counters operate by registering relative movement of the aerosol canister to the dose counter housing, any play or lateral movement can result in false readings being registered on the dose counter. A key factor in the successful operation and functioning of such dose counters is that there be minimal movement of the housing relative to the aerosol canister out with the actuation cycle.

Dimensional variation resulting from manufacturing tolerances of aerosol canisters and dose counter housings poses additional problems in the assembly and operation of medicament dispensers. In order that the dose indicator mechanism functions correctly the canister and the counter housing must fit together tightly. Thus any variations in the dimensions of either of these components which result in a loose fit between the counter housing and the canister can lead to increased relative movement and the problems of false readings discussed above.

To overcome these problems of dimensional variation, stringent tolerance levels must be set for the manufacture of both the counter housing and the aerosol canister. This approach, together with the high levels of quality control necessary to ensure that both components meet the required engineering standards, is expensive for the manufacturer.

It is an object of the present invention to address the aforementioned problems associated with attachment of a mechanical or electrical device to an aerosol canister, in particular for the attachment of a dose counter housing thereto. The present invention involves joining the device housing to a ring or collar affixed around the neck of an aerosol canister to minimise the relative movement of the component parts. This joining can be achieved by a variety of technologies, including melting the components together by means of 'hot staking', soldering the surfaces together, or using adhesives to bind the housing to the collar. Welding technologies are particularly well suited for this purpose.

SUMMARY OF INVENTION

According to the present invention there is provided a housing for a mechanical or electrical device for use with an aerosol canister for containing chemical comprising a sleeve for receipt of the aerosol canister; a collar affixable around the neck of the canister; and a joint between the sleeve and the collar to secure the housing to the canister.

In one aspect, the collar is a split collar.

In another aspect, the collar comprises the same material as the sleeve.

In a further aspect, the joint is a weld.

In yet another aspect, the weld is an ultrasound weld.

In a further aspect, the weld is a single continuous weld.

Optionally the weld comprises a plurality of spot welds. Preferably the number of welds is from 2 to 100, more preferably 6.

In another aspect, the weld is obtainable by energy generated by a sonitrode head, of energy output 100-200 Watts, frequency 20-50 kHz and duration 100-200 milliseconds. A typical sonitrode head would be a converter.

In one aspect, the housing additionally comprises a mechanical or electrical device.

Preferably the mechanical or electrical device is a dose counter.

Preferably the electrical device is a sensor.

Preferably the sensor is for sensing the pressure profile associated with the breath cycle. Pressure transducers are suitable sensors of this type.

More preferably the sensor is for sensing the airflow profile associated with the breath cycle. Sprung vane sensors and sensors including anemometers are suitable sensors of this type.

More preferably the sensor is for sensing the temperature profile associated with the breath cycle. The temperature of the inhaled and exhaled part of the breath cycle varies and may, thus, be used as a measurement tool.

Most preferably the sensor is for sensing the moisture profile associated with the breath cycle. The moisture content of the inhaled and exhaled part of the breath cycle varies and this also may be used as a measurement tool.

In a further aspect, the electrical device comprises a transceiver for transmitting and receiving data. Preferably, the transceiver comprises a radiofrequency identifier comprising an antenna for transmitting or receiving radiofrequency energy, and an integrated circuit chip connecting with said antenna.

The radiofrequency identifier can be any known radiofrequency identifier. Such identifiers are sometimes known as radiofrequency transponders or radiofrequency identification (RFID) tags or labels. Suitable radiofrequency identifiers include those sold by Phillips Semiconductors of the Netherlands under the trade marks Hitag and Icode, those sold by Amtech Systems Corporation of the United States of America under the trade mark Intellitag, and those sold by Texas Instruments of the United States of America under the trade mark Tagit.

Preferably the transceiver comprises a magnetic label or tag comprising an antenna for transmitting or receiving magnetic field energy; and an integrated circuit chip connecting with the antenna.

A suitable magnetic label or tag comprises plural magnetic elements in mutual association whereby the magnetic elements move relative to each other in response to an interrogating magnetic field. A magnetic label or tag of this type is described in U.S. Pat. No. 4,940,966. Another suitable magnetic label or tag comprises a magnetorestrictive element which is readable by application of an interrogating alternating magnetic field in the presence of a magnetic bias field which results in resonance of the magnetorestrictive elements at different predetermined frequencies. A magnetic label of this type is described in PCT Patent Application No. WO92/12402. Another suitable magnetic label or tag comprising plural discrete magnetically active regions in a linear array is described in PCT Patent Application No. WO96/31790. Suitable magnetic labels and tags include those making use of Programmable Magnetic Resonance (PMR) (trade name) technology.

In another aspect, the electrical device comprises a microelectronic memory chip. The microelectronic memory chip may be selected from the group consisting of programmable read only memory (PROM), erasable programmable read only memory (EPROM), electrically erasable programmable read only memory (EEPROM) and a SIM card-type memory chip. The microelectronic memory chip may alternatively be a random access memory (RAM) chip, powered by a suitable source such as a battery.

In one aspect, the housing additionally comprises a window for viewing a reading from the mechanical or electrical device. The reading may typically be in the form of a digital readout on a visual display unit or counter, or may take the form of a flashing coloured light to indicate, for example, the doses remaining within the canister.

In another aspect of the present invention there is provided a method for securing a housing for a mechanical or electrical device to an aerosol canister comprising placing a collar around the neck of the canister; positioning a sleeve around the collar; and joining the collar to the sleeve.

In one aspect, the method additionally comprises associating the mechanical or electrical device with the sleeve. The device may be associated with the sleeve using a snap-fit mechanism. Preferably the method additionally comprises sealing the mechanical or electrical device within the sleeve. The device may be sealed within the sleeve using a range of sealing means, such as welding, soldering or adhesive means. Welding means are particularly suitable for sealing the device within the sleeve.

Preferably the method comprises inserting the mechanical or electrical device into the sleeve before joining the collar to the sleeve. More preferably the method comprises sealing the mechanical or electrical device within the sleeve before joining the collar to the sleeve.

Preferably the method comprises inserting the mechanical or electrical device into the housing after joining the collar to the sleeve. More preferably the method comprises sealing the mechanical or electrical device within the housing after joining the collar to the sleeve.

In one aspect, the device is a dose counter. In another aspect, the device is a sensor. In a further aspect, the device is a transceiver for transmitting or receiving data. In another aspect, the device is a microelectronic memory chip.

In one aspect, the collar is a split collar. Preferably, the collar comprises the same material as the sleeve around the canister.

In another aspect, the method comprises joining the collar to the sleeve by welding. Preferably, the welding comprises ultra sound welding.

More preferably, the method comprises applying a single continuous weld. More preferably, the method comprises applying a plurality of spot welds. More preferably, it comprises applying from 2 to 100 welds, most preferably applying 6 welds.

In a further aspect, the method comprises using a sonitrode head to produce a weld condition of output 100 to 200 Watts, frequency 20 to 50 kilo Hertz and duration 100 to 200 milli seconds.

In another aspect of the present invention there is provided a dispenser comprising a housing according to the invention securable to an aerosol canister.

Preferably the dispenser additionally comprises an actuator body.

Preferably the dispenser is a medicament dispenser wherein the aerosol canister comprises a medicament in a propellant. More preferably the propellant is liquefied HFA134a or HFA-227. Most preferably the medicament is selected from the group consisting of albuterol, salmeterol, ipratropium bromide, fluticasone propionate and beclomethasone dipropionate and salts or solvates thereof and any mixtures thereof.

The present invention further provides a kit of parts comprising a housing according to the present invention and an aerosol canister for containing chemical. Preferably the kit additionally comprising an actuator body. More preferably the chemical is a medicament.

In a further aspect of the present invention there is provided the use of medicament dispenser according to the present invention for the administration of medicament to a patient.

BRIEF DESCRIPTION OF DRAWINGS

The invention will now be described with reference to the accompanying drawings in which.

DETAILED DESCRIPTION OF DRAWINGS

Figure 1:
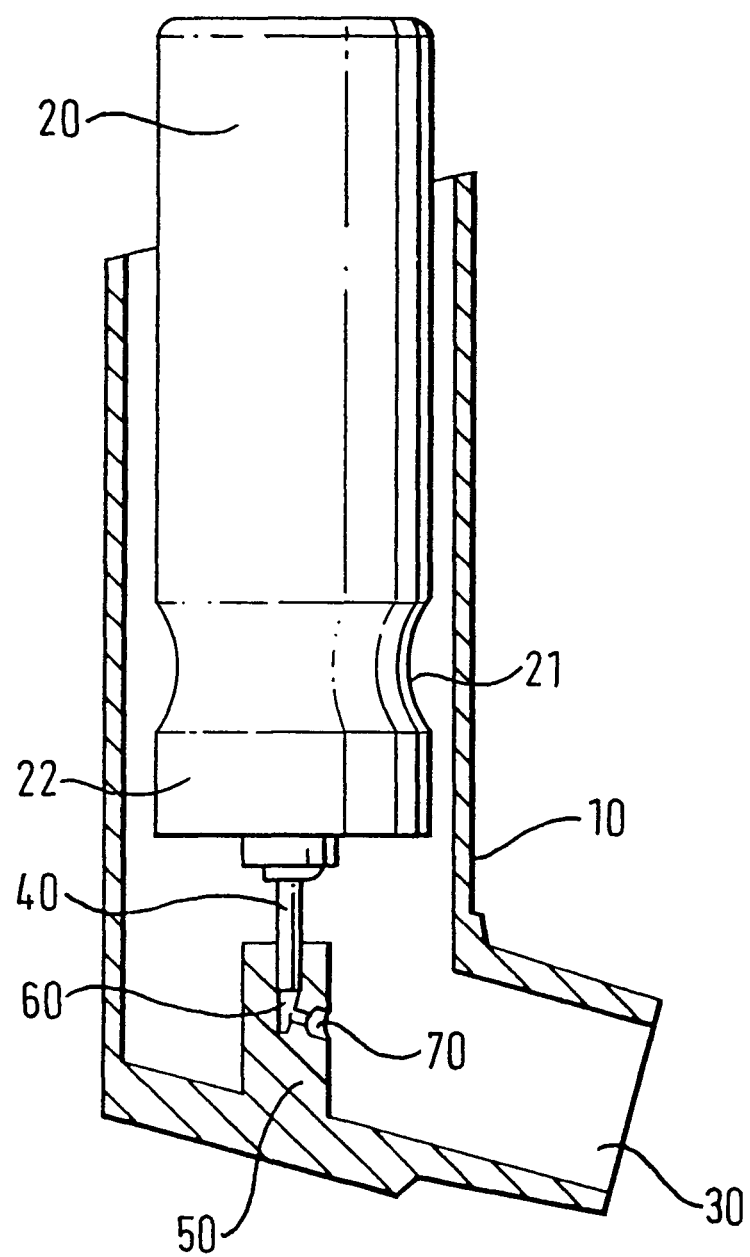
FIG. 1 is a schematic representation of a section through a standard metered dose inhalation device.

The standard metered dose inhaler shown in FIG. 1 comprises a housing 10 in which an aerosol canister 20 can be located. The housing is open at one end (which will hereinafter be considered to be the top of the device for convenience of description) and is closed at the other. An outlet 30 leads laterally from the closed end of the housing 10. In the embodiment illustrated, the outlet 30 is in the form of a mouthpiece intended for insertion into the mouth of the patient but it may, if desired, be designed as a nozzle for insertion into the patient's nostril.

The aerosol canister 20, comprising a neck region 21 and ferrule 22, has an outlet valve stem 40 at one end. This valve member can be depressed to release a measured dose from the aerosol canister or, alternatively, the valve stem 40 can be fixed and the main body of the canister can be moved relative to the valve member to release the dose.

As shown in FIG. 1, the aerosol canister 20 is located in the housing 10 so that one end protrudes from its open top, the canister being positioned such that the neck 21 and valve ferrule 22 are enclosed within housing 10. Spacer ribs (not shown) may be provided inside the housing to hold the external surface of the canister 20 spaced from the internal surface of the housing 10. A support 50 is provided at the lower end of the housing 10 and has a passage 60 in which the valve stem 40 of the aerosol canister 20 can be located and supported. A second passage 70 is provided in the support 50 and is directed towards the interior of the outlet 30. Thus, when the parts are in the positions shown in FIG. 1, the protruding portion of the aerosol canister 20 can be depressed to move the canister relative to the valve stem 40 to open the valve and a dose of medicament contained in the aerosol will be discharged through the passage 70 and into the outlet 30 from which it can be inhaled by a patient. One dose will be released from the aerosol canister each time it is fully depressed.

Figure 2:
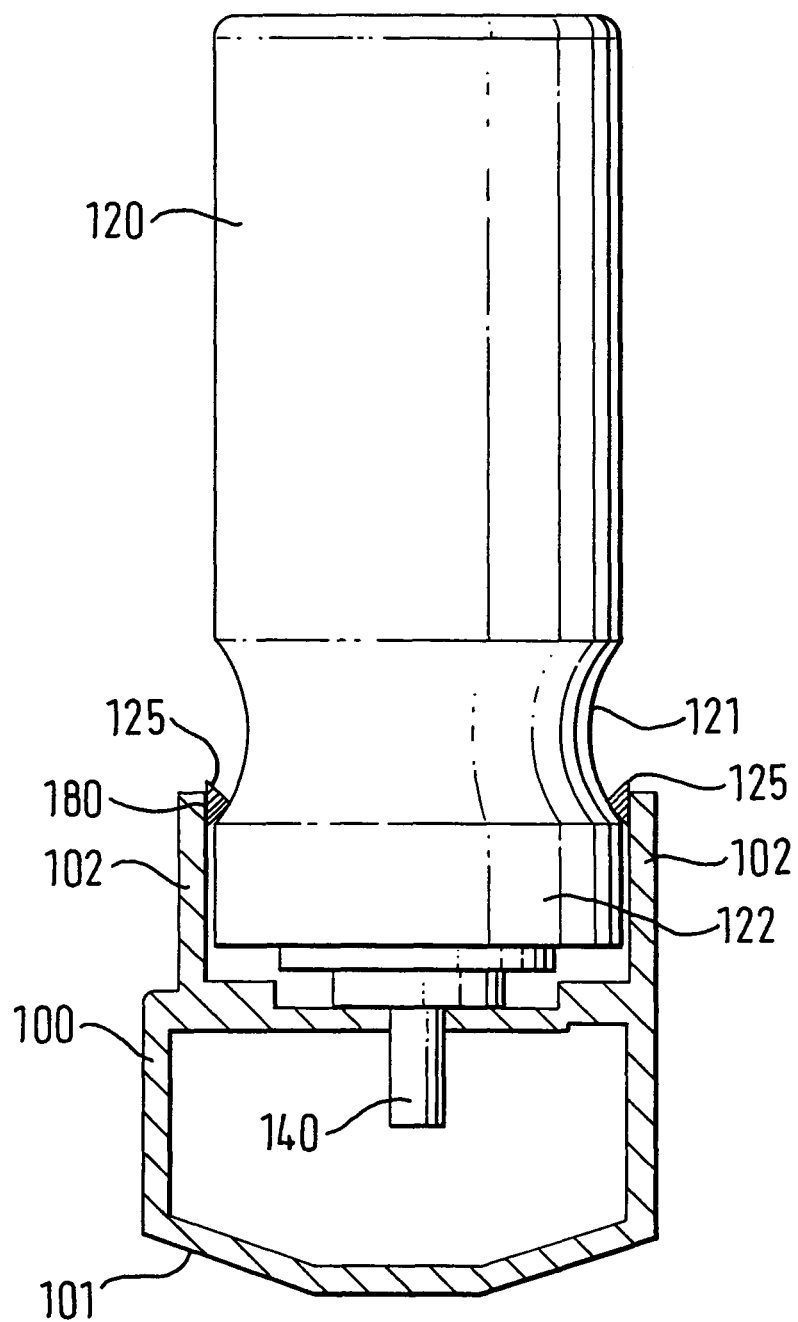
FIG. 2 is a schematic representation of a section through an aerosol canister affixed to a housing according to the present invention.

FIG. 2 is a schematic diagram showing a housing for a dose indicating device 100 (internal details not shown) connected to an aerosol canister 120 according to the present invention. The housing comprises a cradle 101 for supporting the counter mechanism, located within the body of the counter (details not shown), and a housing 100 having a tubular sleeve 102 to receive aerosol canister 120 and valve stem 140. Collar 125, which is typically a split ring, is secured around the neck 121 of the aerosol canister 120. Tubular sleeve 102 fits over valve ferrule 122 and engages collar 125 which is tightly affixed around neck 121 of aerosol canister 120. Thus the tubular sleeve 102 and collar 125 form a tight connection between housing 100 and aerosol canister 120. Collar 125 is welded to sleeve 102 by application of ultrasound energy. The sleeve 102 is secured to the collar 125 by a series of spot welds 180. Two sonitrodes (not shown) are generally employed in the welding process, each sonitrode having three pins which are pushed into contact with the sleeve 102. Energy is transferred through the sonitrode pins, causing them to vibrate and fusing the sleeve 102 to the collar 125. The vibrating pins are pushed through the sleeve 102 to a depth of approximately 2 mm into the body of the collar 125, melting and fusing the materials together, to form a series of spot welds. In an alternative herein, one continuous weld may be employed by either moving the sonitrode head around the sleeve or vice versa.

Figure 3:
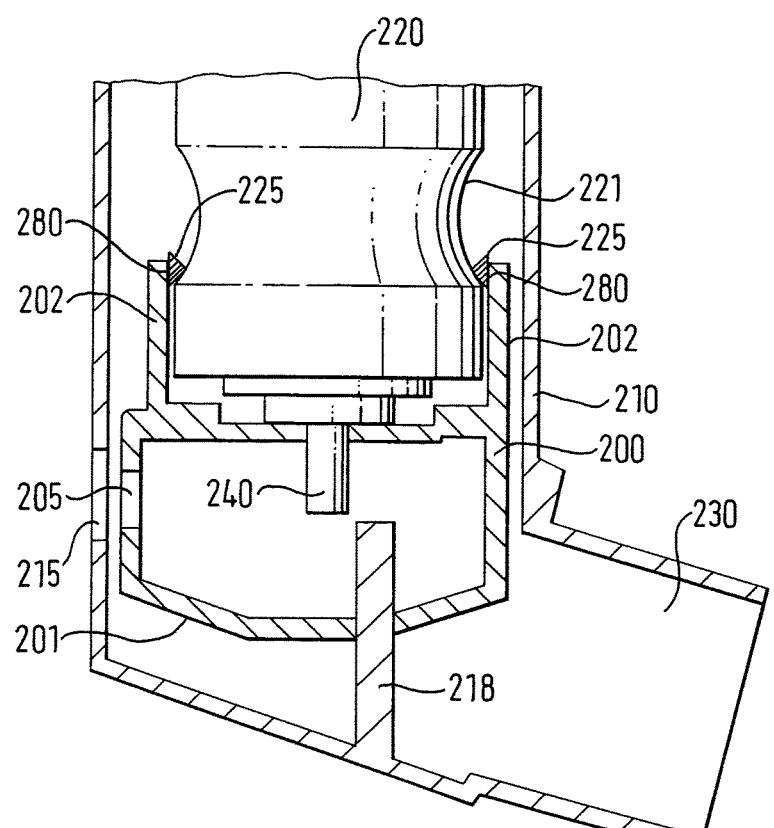
FIG. 3 is a schematic representation of a medical dispenser according to the present invention.

FIG. 3 is a schematic diagram showing the lower part of a device similar to that of FIG. 1 but incorporating the housing for a dose indicating device 200 affixed to an aerosol canister according to the invention as shown in FIG. 2. The counter mechanism (not shown) is supported on a cradle 201 and engages post 218. Ultrasound welds 280 secure collar 225 around neck 221 of canister 220 to tubular sleeve 202, thereby affixing aerosol canister 220 to dose counter housing 200. The resulting assembly is positioned within housing 210. Thus on depression of the aerosol canister 220, the canister moves relative to the valve stem 240 and opens the canister valve (not shown) to discharge a predetermined dose of medicament to the patient through valve stem 240 and thence to outlet 230. The relative movement of canister 220 to counter housing 200 is registered by the counter mechanism (not shown) and the number of doses of medicament used or remaining within canister 220 is displayed on counter window 205 and can be viewed through housing window 215.

Figure 4A:
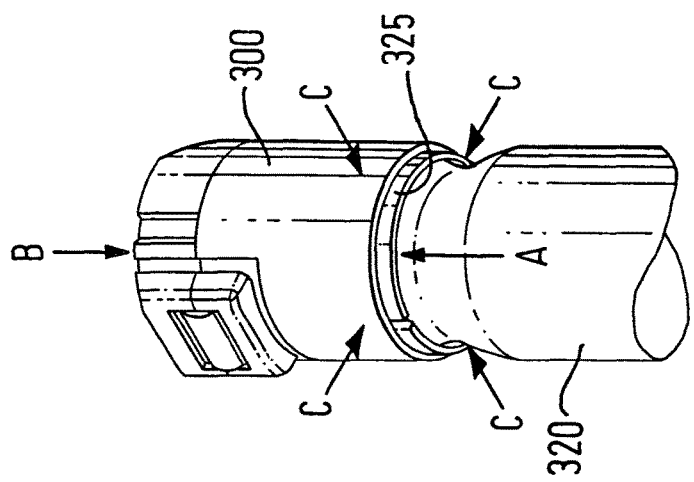
FIGS. 4a-c is a schematic illustration of the process whereby a dose counter housing is secured to a standard metered dose inhalation device by ultrasound welding.
Figure 4B:
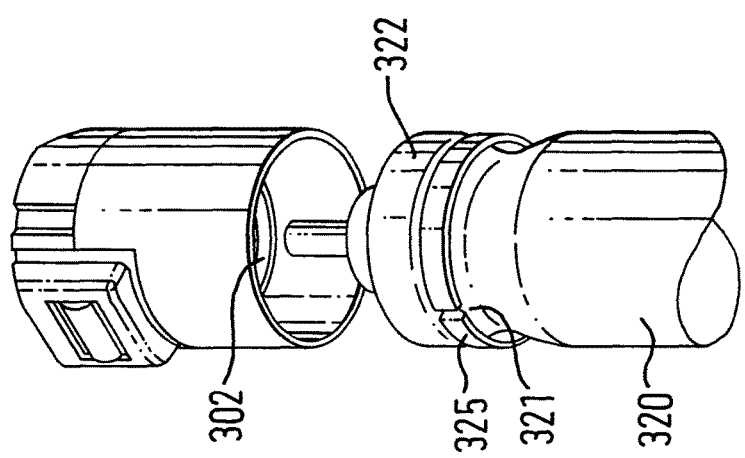
Figure 4C:
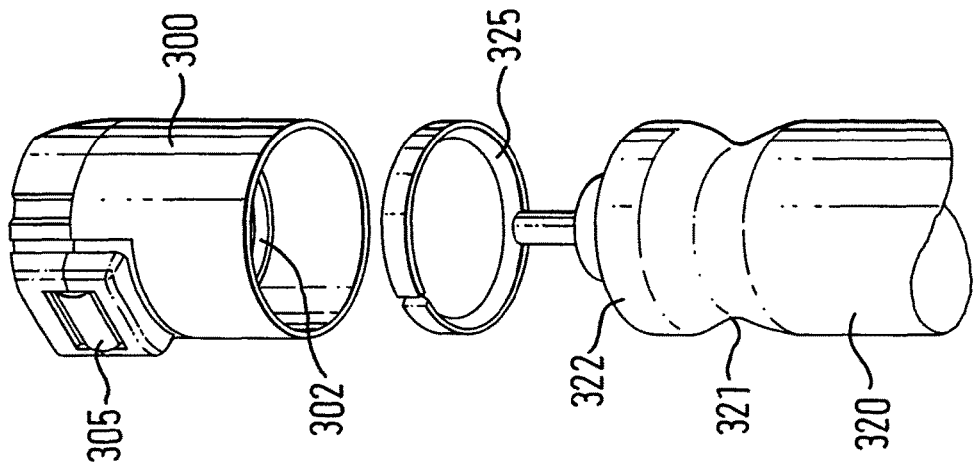

FIGS. 4a-c illustrate, with another embodiment of the present invention, the process whereby the collar 325 is fitted around neck 321 of the canister 320 and welded to tubular sleeve 302 of the dose counter housing 300. FIG. 4a is an exploded diagram showing collar 325 being positioned between canister 320 and dose counter housing 300 displaying counter window 305. The collar 325 is slipped around neck 321 of canister 320 (FIG. 4b). As shown in FIG. 4c, the collar 325 is then pushed in the direction of arrow A to locate against the base of ferrule 322 at the top of neck 321, while dose counter housing 300 is positioned over the top of canister 320 by being pressed down in the direction of arrow B. In this way, collar 325 is wedged between tubular sleeve 302 and the neck of canister 321. The collar 325 is joined to tubular sleeve 302 by ultra sound welding at the points indicated by arrows C, thereby securing the dose counter housing 300 to canister 320.

Figure 5B:
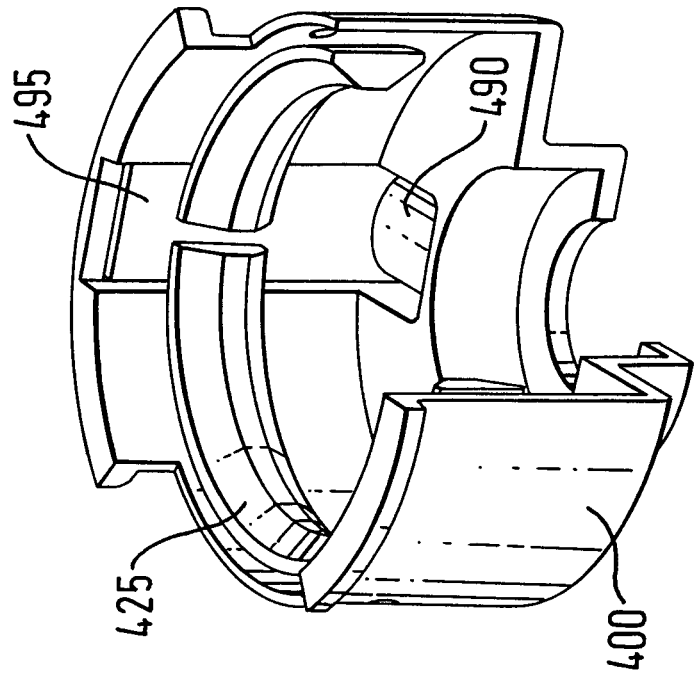
FIGS. 5a & b show a housing for a transceiver affixed to an aerosol container and a cross section of the housing according to the present invention.
Figure 5A:
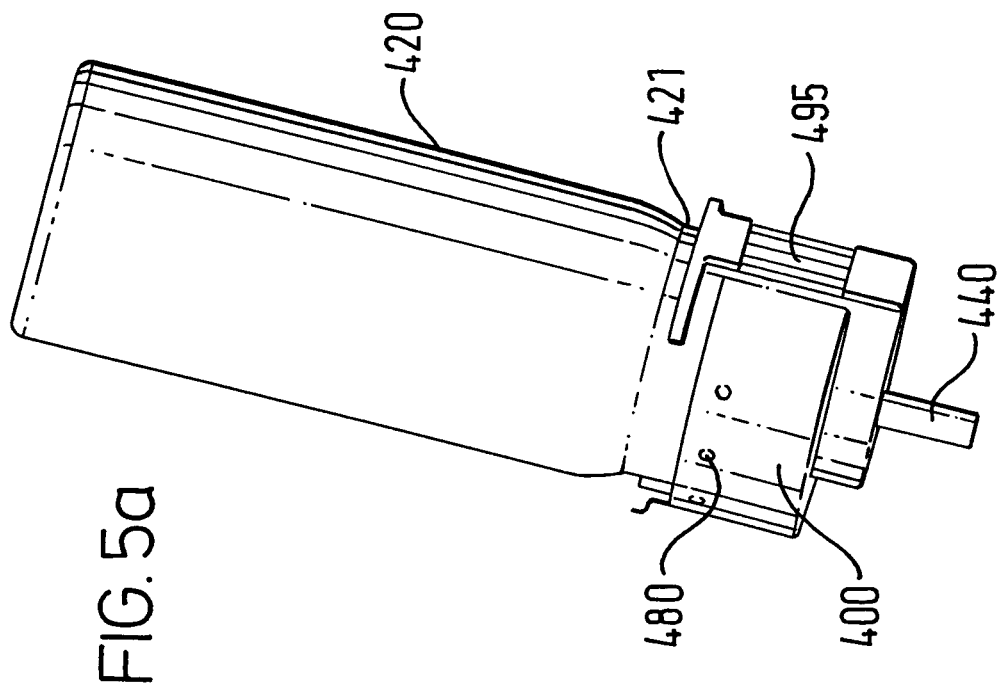

FIGS. 5a and 5b show a housing 400 for a passive transceiver in the form of an electrically erasable programmable read only memory (EEPROM) chip 490. In FIG. 5a the housing 400 is welded at points 480 to collar 425 (not shown) which has been secured to the neck 421 of the aerosol canister 420 having outlet 440 as described above. The chip 490, located within housing 400, communicates with electrical contact pad 495. FIG. 5b is a cut-away section of FIG. 5a, the aerosol canister having been removed to show collar 425 welded to housing 400. In this sectional view, EEPROM chip 490 and electrical contact pad 495 are clearly shown.

Whilst the present invention has been described in detail in respect of a metered dose inhaler it will be appreciated that other mechanical and electronic devices, such as electronic sensors and readers, may be attached to an aerosol canister in an identical manner. For example, a temperature/pressure sensor for use with a paint dispenser could also be affixed to the aerosol canister in this way.

It may be appreciated that any of the parts of the dispenser which contact the chemical suspension may be coated with materials such as fluoropolymer materials which reduce the tendency of chemical to adhere thereto. Any movable parts may also have coatings applied thereto which enhance their desired movement characteristics. Frictional coatings may therefore be applied to enhance frictional contact and lubricants used to reduce frictional contact as necessary.

The medicament dispenser of the invention is suitable for dispensing medicament, particularly for the treatment of respiratory disorders such as asthma and chronic obstructive pulmonary disease. Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (e.g. s the sodium salt), ketotifen or nedocromil (e.g. as the sodium salt); antiinfectives e.g., cephalosporins, penicillins, streptomycin, sulphonamides, tetracyclines and pentamidine; antihistamines, e.g., methapyrilene; anti-inflammatories, e.g., beclomethasone (e.g. as the dipropionate ester), fluticasone (e.g. as the propionate ester), flunisolide, budesonide, rofleponide, mometasone e.g. as the furoate ester), ciclesonide, triamcinolone (e.g. as the acetonide) or 6α,9α-difluoro-11β-hydroxy-16α-methyl-3-oxo-17α-propionyloxy-androsta-1,4-diene-17β-carbothioic acid S-(2-oxo-tetrahydro-furan-3-yl) ester; antitussives, e.g., noscapine; bronchodilators, e.g., albuterol (e.g. as free base or sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol or 4-hydroxy-7-[2-[[2-[[3-(2-phenylethoxy)propyl]sulfonyl]ethyl]amino]ethyl-2(3H)-benzothiazolone; adenosine 2a agonists, e.g. 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3, 4-diol (e.g. as maleate); α4 integrin inhibitors e.g. (2S)-3-[4-({[4-(aminocarbonyl)-1-piperidinyl]carbonyl}oxy) phenyl]-2-[((2S)-4-methyl-2-{[2-(2-methylphenoxy)acetyl] amino}pentanoyl)amino]propanoic acid (e.g. as free acid or potassium salt), diuretics, e.g., amiloride; anticholinergics, e.g., ipratropium (e.g. as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament and/or to minimise the solubility of the medicament in the propellant. Preferred medicaments are selected from albuterol, salmeterol, fluticasone propionate and beclomethasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) or formoterol (e.g. as the fumarate salt) in combination with an antiinflammatory steroid such as a beclomethasone ester (e.g., the dipropionate) or a fluticasone ester (e.g., the propionate) or budesonide. A particularly preferred combination is a combination of fluticasone propionate and salmeterol, or a salt thereof (particularly the xinafoate salt). A further combination of particular interest is budesonide and formoterol (e.g. as the fumarate salt).

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims:

The invention claimed is:

1. An assembly comprising:
   (a) a container configured to contain a product, the container having:
      (i) an end having a dispensing end surface,
      (ii) a central axis which extends through the end; and
      (iii) a neck underneath the end, the neck having a neck outer surface which tapers outwardly away from the central axis as it extends in a direction towards the end;
   (b) an accessory, comprising a dose counter, non-removably mounted on the end of the container, the accessory having:
      (i) a surface bearing against the dispensing end surface of the container, and
      (ii) a sleeve, comprising a sleeve inner surface, disposed about the neck so that the sleeve inner surface is in facing relation with the neck outer surface; and
   (c) an annular collar wedged between the sleeve inner surface and the neck outer surface and joined to the sleeve inner surface by a permanent joint; and
   wherein the accessory is immovable axially with respect to the container,
   wherein the end is an outlet end of the container having an outlet through which the product is able to be dispensed from the container, and
   wherein the container is a dispensing container for a fluid product and the outlet is configured to dispense measured doses of the fluid product from the container when present therein.

2. An assembly comprising:
(a) a container configured to contain a product, the container having:
   (i) an end having a dispensing end surface,
   (ii) a central axis which extends through the end; and
   (iii) a neck underneath the end, the neck having neck outer surface which tapers outwardly away from the central axis as it extends in a direction towards the end;
(b) an accessory, comprising a dose counter, non-removably mounted on the end of the container, the accessory having:
   (i) a surface bearing against the dispensing end surface of the container, and
   (ii) a sleeve, comprising a sleeve inner surface, disposed about the neck so that the sleeve inner surface is in facing relation with the neck outer surface; and
(c) an annular collar wedged between the sleeve inner surface and the neck outer surface and joined to the sleeve inner surface by a permanent joint; and wherein the accessory is immovable axially with respect to the container, wherein the end is an outlet end of the container having an outlet through which the product is able to be dispensed from the container, wherein the container is a dispensing container for a fluid product and the outlet is configured to dispense measured doses of the fluid product from the container when present therein, wherein the dispensing container is an aerosol container and the outlet is a valve, and wherein the aerosol container contains a medicament in a propellant.

3. The assembly of claim 2, wherein the dispensing end surface is presented by a ferrule.

4. The assembly of claim 3, wherein the ferrule presents at least part of the neck outer surface and the collar is wedged against the ferrule.

* * * * *